United States Patent [19]

Sugiyama et al.

[11] Patent Number: 4,955,895
[45] Date of Patent: Sep. 11, 1990

[54] VASODILATING CATHETER

[75] Inventors: Yoshiaki Sugiyama; Kyuta Sagae, both of Fuji, Japan

[73] Assignee: Terumo Kabushiki Kaisha, Tokyo, Japan

[21] Appl. No.: 382,781
[22] PCT Filed: Dec. 22, 1987
[86] PCT No.: PCT/JP87/01013
  § 371 Date: Jun. 22, 1989
  § 102(e) Date: Jun. 22, 1989
[87] PCT Pub. No.: WO88/04560
  PCT Pub. Date: Jun. 30, 1988

[30] Foreign Application Priority Data

Dec. 23, 1986 [JP] Japan .................. 61-305385

[51] Int. Cl.$^5$ ............................ A61M 29/00
[52] U.S. Cl. ..................... 606/194; 604/96; 604/102; 604/104; 606/191; 606/194
[58] Field of Search ............. 604/96, 97, 98, 102, 604/103, 104; 606/191, 192, 194

[56] References Cited

U.S. PATENT DOCUMENTS

| 4,195,637 | 4/1980 | Grüntzig et al. | 604/53 |
| 4,323,071 | 4/1982 | Simpson et al. | 604/53 X |
| 4,819,751 | 4/1989 | Shimada et al. | 604/104 X |

Primary Examiner—Mickey Yu
Assistant Examiner—Beth Anne Cicconi
Attorney, Agent, or Firm—Frishauf, Holtz, Goodman & Woodward

[57] ABSTRACT

A vasodilating catheter is disclosed which is characterized by using a triple-flow catheter tube and allowing two of the three flow paths formed by the catheter tube to communicate with a balloon. Owing to this configuration, the air entrapped inside the balloon can be easily removed and, as the result, the otherwise inevitable degradation of the balloon's opacitying property is precluded and the angioplasty is performed with increased safety and ease.

19 Claims, 5 Drawing Sheets

VASODILATING CATHETER

DESCRIPTION

1. Technical Field:

This invention relates to a vasodilating catheter. More particularly, this invention relates to a vasodilating catheter for curatively dilating a stenosis in a blood vessel and improving the flow of blood on the peripheral blood vessel.

2. Background Art:

When a stenosis or an obstruction occurs in a vessel such as the blood vessel, a suitable form of angioplasty (such as percutaneous transluminal angioplasty [PTA-]or percutaneous transluminal coronary angioplasty [PTCA]) is performed for the purpose of widening the stenotic site or reopening the obstructed site of the vessel and improving the flow of body fluid on the peripheral vessel. The angioplasty is effected, for example, by first securing percutaneously the blood vessel in trouble, inserting a thin guide wire into the vessel, allowing a catheter provided at the leading end thereof with a balloon to be inserted into the vessel as led by the guide wire, locating the balloon at the point of stenosis or obstruction, and subsequently injection a liquid (such as, for example, an contrast medium or physiological saline solution) through a terminal hub into the balloon under application of pressure (on the order of several to 10 atmospheres) thereby inflating the balloon toward and against the inner wall of the vessel and consequently expanding the stenotic or obstructed site of the vessel with pressure.

The vasodilating catheters heretofore used for various forms of angioplasty fall mainly under the GRÜNTZIG type and the Simpson-Robert type. The catheters of the GRÜNTZIG type have a general construction which comprises a catheter tube possessed of two tubular cavities and provided near the leading end thereof with a balloon and adapts one of the two tubular cavities to open at the leading end thereof and form a passage for a guide wire and for measurement of the leading end pressure and the other tubular cavity to communicate with the balloon at the basal side of the balloon and form a flow path for pressure injection such as of a contrast medium intended for the inflation of the balloon. The catheters of the Simpson-Robert type share a coaxial double-flow construction which comprises an inner tube opening at the leading end thereof and forming a first flow path, an outer tube encircling the inner tube, defining a second flow path jointly with the inner tube, and continuing at the leading end thereof into a balloon, and very thin metallic pipe adapted for removal of bubbles and disposed inside the second flow path. The catheters of this type, therefore, are put to use in the angioplasty after the contrast medium has been injected into the balloon through the second flow path and the residual air removed through the metallic pipe.

The catheters of the GRÜNTZIG type, however, have disadvantage that the bubbles which survive inside the balloon when the balloon in inflated by pressure injection of the contrast medium necessitate a complicated work for their removal and even defy all efforts to effect their thorough removal and, as the result, the opacifying property of the balloon is degraded so much as to render difficult perfect recognition of the position and shape of the inflated balloon and impede perfect executing of the angioplasty. Worse still, owing to the configuration of the catheter tube which requires incorporation of the two tubular cavities, the catheter is devoid of flexibility and is liable to injure the inner wall of the blood vessel which normally abounds with bends.

The catheters of the Simpson-Robert type likewise have a disadvantage that owing to the metallic pipes used for the removal of bubbles, the catheter is devoid of flexibility and, similarly to the catheters of the GRÜNTZIG type, is liable to injure the inner wall of the blood vessel abounding with bends and the metallic pipe itself is apt to pierce the catheter.

An object of this invention is to provide a novel vasodilating catheter. Another object of this invention is to provide a vasodilating catheter which permits easy removal of entrapped air from inside a balloon and, consequently, prevents the opacifying property of the balloon from being degraded by survival of bubbles, and facilitates recognition of the position and shape of the inflated balloon inside the blood vessel. A further object of this invention is to provide a vasodilating catheter which represses damage of the inner wall of the blood vessel and precludes complication of the separation of the internal membrane of the blood vessel, for example.

SUMMARY OF INVENTION

The objects described above are accomplished by a vasodilating catheter which comprises a triple-flow catheter tube comprising an inner tube opening at the leading end thereof and defining a first flow path, a middle tube encircling the inner tube and defining a second flow path jointly with the inner tube, and an outer tube encircling the middle tube and defining a third flow path jointly with the middle tube, an at least partially cylindrical foldable balloon attached to the outer periphery of the catheter tube so as to enclose therewith the openings of the second flow path and the third flow path in the proximity of the leading end of the catheter tube and form a space communicating with the second flow path and the third flow path, and three ports communicating with the three flow paths mentioned above, attached to the basal end of the catheter tube.

This invention also discloses a vasodilating catheter wherein the opening of the second flow path is formed in the proximity of one end of the balloon and the opening of the third flow path in the proximity of the other end of the balloon. This invention further discloses a vasodilating catheter wherein the opening of the second flow path is formed in the proximity of the catheter tube's leading end side terminal of the balloon and the opening of the third flow path in the proximity of the catheter tube's basal side terminal of the balloon. This invention also discloses a vasodilating catheter wherein the middle tube is provided on the inner peripheral surface thereof with at least one protuberance contiguous to the outer peripheral surface of the inner tube. This invention further discloses a vasodilating catheter wherein the leading end of the middle tube is tapered to a diameter equal to or slightly smaller than the outside diameter of the inner tube and fitted into the inner tube and fastened thereto with an adhesive agent or by thermal fusion and the second flow path is allowed to communicate with the balloon through the medium of at least one lateral hole formed in the middle tube near the leading end thereof. This invention also discloses a vasodilating catheter wherein the leading end of the outer tube is tapered to a diameter equal to or slightly smaller than the outside diameter of the middle tube and fitted into the middle tube and fastened thereto with an adhesive agent or by thermal fusion and the third flow path is allowed to communicate with the balloon through the medium of at least one lateral hole formed in the outer tube near the leading end thereof. Further this invention discloses a vasodilating catheter wherein the inner tube, the middle tube, and the outer tube of the triple-flow catheter tube are disposed coaxially relative to one another. This invention also discloses a vasodilating catheter wherein the triple-flow catheter tube and the balloon are formed with thermoplastic resin. This invention further discloses a vasodilating catheter wherein the hardness of the balloon is lower than that of the triple-flow catheter tube. This invention also discloses a vasodilating catheter wherein the outer surface of the outer tube, the outer surface of the balloon, and the inner surface of the inner tube have undergone a treatment for impartation of hydrophilicity.

BEST MODE FOR CARRYING OUT THE INVENTION

This invention is directed to a vasodilating catheter which is characterized saliently by using a catheter tube of a triple-flow construction and allowing two of the three flow paths formed by this particular catheter tube to communicate with a balloon. In the vasodilating catheter of this invention, therefore, when the balloon is disposed at a prescribed position and this balloon is inflated by injection of an contrast medium through a terminal adapter, the air entrapped within the balloon is easily discharged via one of the flow paths communicating with the balloon as the contrast medium is advanced via the other flow path into the balloon. As the result, the degradation of the opacifying property of the balloon to be induced when bubbles persist in the contrast medium held inside the balloon is precluded and the recognition of the position and the shape of the inflated balloon inside the blood vessel is facilitated. The vasodilating catheter, therefore, enables the angioplasty to be performed safely and easily and curbs infliction of injury to the inner wall of the blood vessel and represses complication of the separation of the inner membrane of the blood vessel. Further in the vasodilating catheter of this invention, since the flow path for removal of bubbles is formed by one of the flow paths which are defined by the walls of the triple-flow catheter tube, the vasodilating catheter is allowed to retain its flexibility intact and has no possibility of inflicting injury to the inner wall of the blood vessel even when the blood vessel happens to abound with bends.

Now, the vasodilating catheter of the present invention will be described more specifically below with reference to embodiments. It should be noted, however, that these embodiments are cited exclusively aiding in explanation of the invention and are not meant in any way to limit the scope of this invention.

Figure 1:
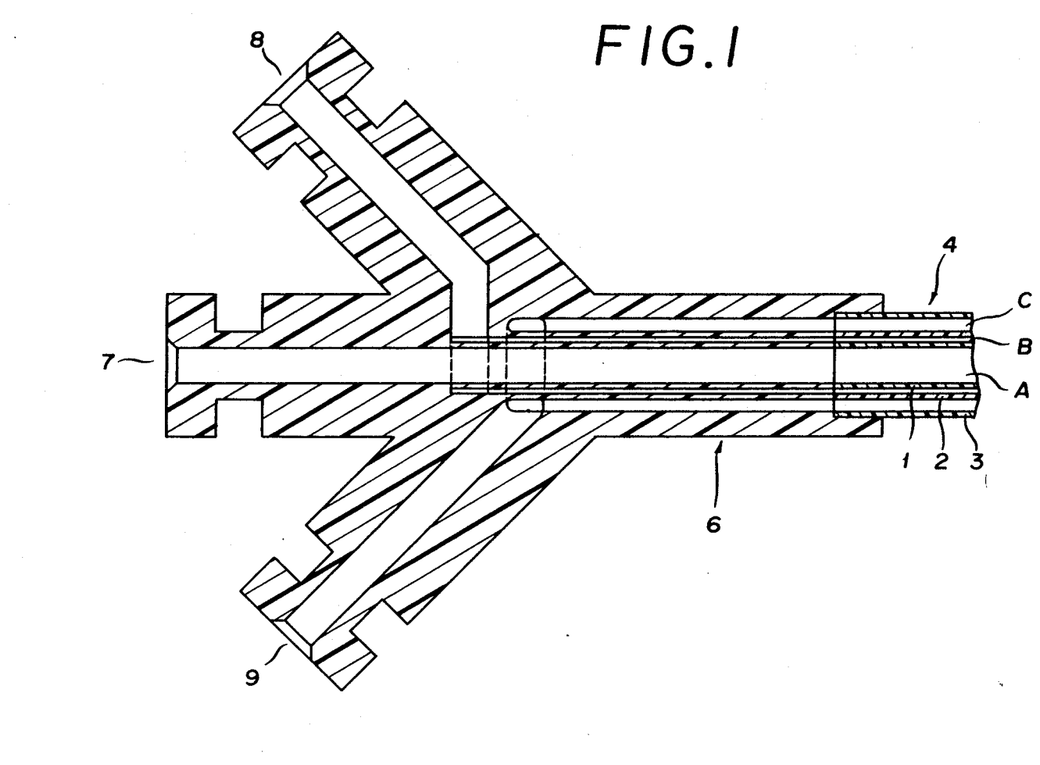
FIG. 1 is a magnified cross section illustrating the construction of the basal end part of a typical vasodilating catheter as one embodiment of this invention.
Figure 2:
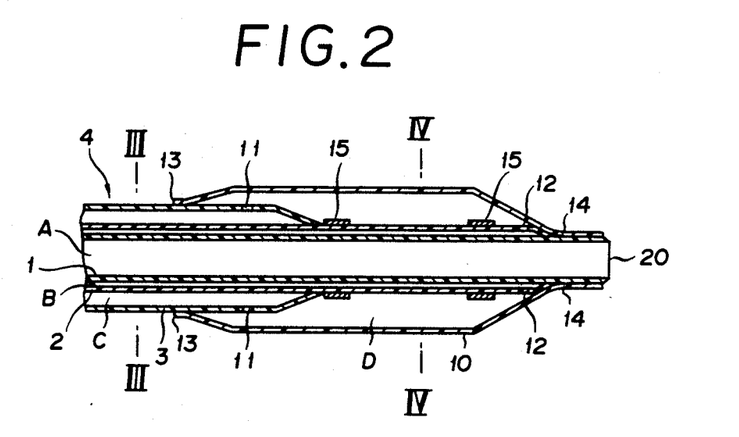
FIG. 2 is a magnified cross section illustrating the construction of the leading end part of the same vasodilating catheter.
Figure 3:
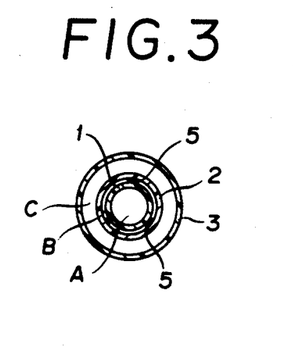
FIG. 3 is a cross section taken through FIG. 2 along the line III—III.
Figure 4:
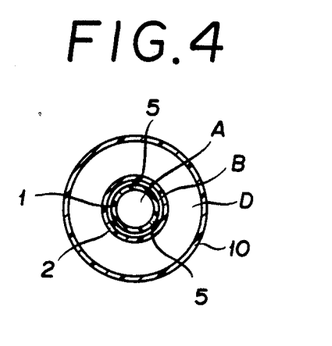
FIG. 4 is a cross section taken through FIG. 2 along the line IV—IV.

FIG. 1 through FIG. 4 illustrate a typical vasodilating catheter as one embodiment of this invention. FIG. 1 is a magnified cross section illustrating the construction of the basal end side of the present embodiment. FIGS. 2 through 4 are magnified cross sections illustrating the construction on the leading end side of the present embodiment.

Specifically as illustrated in FIGS. 1 through 4, the vasodilating catheter of the present invention uses as a catheter tube a triple-flow type catheter tube 4 which is composed of an inner tube 1 opening at the leading end thereof and defining a first flow path A, a middle tube 2 encircling the inner tube 1 and defining a second flow path B jointly with the inner tube 1, and an outer tube 3 encircling the middle tube 2 and defining a third flow path C jointly with the middle tube 2.

In the present embodiment, the first flow path A functions as a path for blood and as a route for a guide wire during the use of the vasodilating catheter, the second flow path B as a path for discharge of entrapped air, and the third flow path C as a path for injection of an contrast medium. The cross-sectional area of the second flow path B, therefore, is desired to be smaller than that of the third flow path C. In another embodiment of this invention, it is allowed conversely to form the second flow path B as a path for injection of the contrast medium and the third flow path C as a path for discharge of the entrapped air. In this embodiment, the cross-sectional area of the second flow path B is desired to be larger than that of the third flow path C.

Further in the vasodilating catheter of the present invention, the inner tube 1, the middle tube 2, and the outer tube 3 which jointly make up the triple-flow catheter tube 4 are desired to be disposed coaxially relative to one another. Optionally, however, they may be disposed otherwise on condition that the individual flow paths are sufficiently secured and the ample flexibility of the catheter tube is not impaired. For example, the inner tube 1 and the outer tube 3 may be formed with circular cross sections and the middle tube 2 with an elliptic cross section and they may be disposed so that the axes of the former two tubes and the center line of the latter tube will substantially coincide with one another.

In the present invention, the outside diameter of the inner tube 1 and the inside diameter of the middle tube 2 are approximated to each other so as to give a small cross-sectional area to the second flow path B which functions as the path for discharge of the entrapped air. For the purpose of preventing the inner tube 1 and the middle tube 2 from coming into intimate mutual contact and blocking the second flow path B, the middle tube 2 is provided on the inner peripheral surface thereof with protuberances 5 contiguous with the outer peripheral surface of the inner tube. In the embodiment using such protuberances 5, the number of these protuberances 5 is desired to exceed 2, preferably to fall in the range of 2 to 4. These protuberances may be formed like bars running in the direction of the axis or dots regularly spaced. Of course, the effect of the provision of these protuberances is attained by having the protuberances formed on the outer peripheral surface.

In the vasodilating catheter of this embodiment of this invention, the triple-flow catheter tube 4 constructed as described above is provided at the basal end thereof with a three-way adapter 6 as illustrated in FIG. 1. The three ports incorporated in the three-way adapter 6 severally communicate with the three flow paths formed by the triple-wall type catheter tube 4. In the present embodiment, a guide wire port 7 of the three-way adapter 6 communicates with the first flow path A, a vent port 8 thereof with the second flow path B, and an injection port 9 thereof with the third flow path C respectively.

Figure 5:
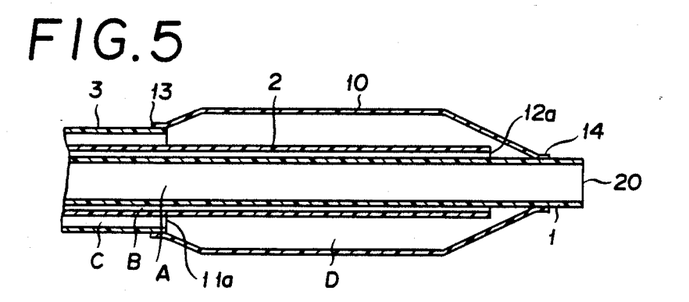
FIG. 5 through FIG. 7 are magnified cross sections illustrating the constructions of the leading end parts of other vasodilating catheters as other embodiments of this invention.
Figure 6:
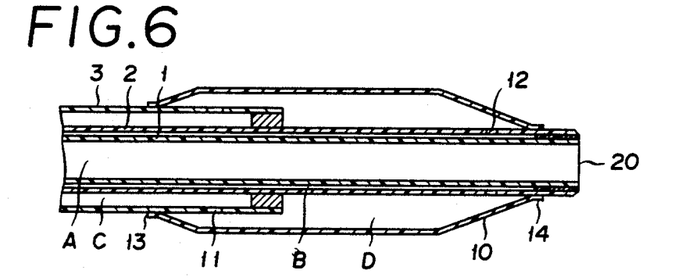
Figure 7:
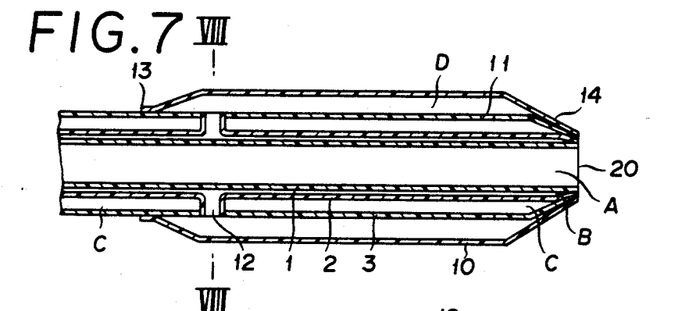
Figure 8:
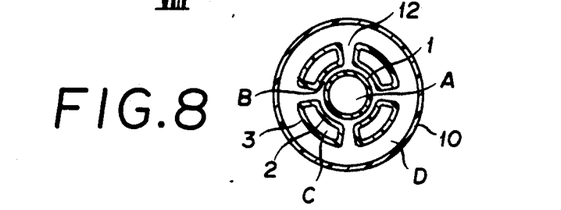
FIG. 8 is a cross section taken through FIG. 7 along the line VIII—VIII.

In the proximity of the leading end of the vasodilating catheter of this invention, an inflatable and shrinkable balloon 10 is attached to the outer periphery of the triple-flow catheter tube 4, preferably in a cylindrical shape coaxial with the catheter tube as illustrated in FIG. 2 and FIG. 4. In the vasodilating catheter of this invention, the balloon 10 must be constructed in such a manner as to enclose therewith the openings of the second flow path B and the third flow path C and form a closed space D communicating jointly with the second flow path B and the third flow path C. In the present embodiment, for example, the leading end portion of the triple-flow catheter tube 4 is so constructed that the leading end of the outer tube 3 is tapered to a diameter equal to or slightly smaller than the outside diameter of the middle tube 2 and fitted into the middle tube 2 and fastened thereto with an adhesive agent or by thermal fusion, the middle tube 2 which is extended farther from the leading end of the outer tube 3 is similarly tapered to a diameter equal to or slightly smaller than the outside diameter of the inner tube 1 and fitted into the inner tube and fastened thereto with an adhesive agent or by thermal fusion, and the outer tube 3 and the middle tube 2 are severally provided slightly on basal sides thereof from the fastened positions mentioned above with lateral holes 11, 12 at least one each as illustrated in FIG. 2. In this arrangement, therefore, the balloon 10 is attached to the outer periphery of the triple-flow catheter tube by fastening one end part 13 of the balloon 10 on the outer periphery of the outer tube 3 farther toward the basal end side of the outer tube 3 than the lateral hole 11 with an adhesive agent or by thermal fusion and fastening the other end part 14 of the balloon 10 to the outer periphery of the middle tube 2 or the inner tube 1 farther toward the leading end side of the middle tube 2 than the lateral hole 12 with an adhesive agent or by thermal fusion. The construction of the leading end portion of the triple-flow catheter tube 4 (such as the disposition of the openings of the middle tube 2 and the outer tube 3) and the construction of the balloon 10 in terms of union thereof with the catheter tube 4 need not be limited to those of the present embodiment but may be altered variously so long as the balloon 10 is allowed to enclose therewith the openings of the second flow path B and the third flow path C and form a closed space D communicating with the second flow path B and the third flow path C. For example, the constructions such as are illustrated in FIG. 5, FIG. 6, and FIGS. 7 and 8 are applicable to the design of the leading end portion of the vasodilating catheter of the present invention. The reference symbols indicated in FIGS. 5 through 8 represent the same components as indicated by the same reference symbols in FIG. 2. In FIG. 5, the reference symbols 11a and 12a denote the opening ends of the outer tube and the middle tube respectively.

In the vasodilating catheter of the present invention, for the purpose of ensuring efficient discharge of the entrapped air from within the balloon 10 by the injection of the contrast medium, the openings (lateral holes 11 and 12 or the opening ends 11a, 12a) of the second flow path B and the third flow path C enclosed with the balloon 10 as described above are desired to be so disposed that, as in the embodiments illustrated in FIG. 2, FIG. 5, FIG. 6, or FIGS. 7 and 8, the opening in either of the flow paths will be located in the proximity of one end part 13 of the balloon and the opening in the other flow path in the proximity of the other end part 14 of the balloon. In view of the construction of the coaxial triple-flow catheter tube which gives rise to the second flow path B and the third flow path C, it is desirable for the sake of ease of fabrication to have the opening (lateral hole 11 or opening end 11a) of the third flow path C in the proximity of the end part 13 of the balloon 10 on the basal end side of the catheter tube and the opening (lateral hole 12 or opening end 12a) of the second flow path B in the proximity of the end part 14 of the balloon 10 or the leading end side of the catheter tube.

In the vasodilating catheter of the present embodiment illustrated in FIG. 1 through FIG. 4, markers 15 impervious to X-ray are attached or fastened to the middle tube inside the balloon 10, one in the proximity of the middle tube's 2 basal end side of the lateral hole 12 and the other in the proximity of the leading end side portion of the part of tight union between the middle tube 2 and the outer tube 3, so as to permit recognition of the position of the balloon 10 under observation with X-ray.

The vasodilating catheter of the present invention is constructed as described above. As concerns the materials used for the construction, a thermoplatic resin such as, for example, polyvinyl chloride, polypropylene, polyethylene, or ethylene-vinyl acetate copolymer or a synthetic rubber such as ethylene-propylene rubber or silicone rubber may be used for the triple-flow catheter tube made up of the inner tube 1, the middle tube 2, and the outer tube 3, a thermoplastic resin such as flexible polyvinyl chloride, polypropylene, polyethylene, or ethylene-vinyl acetate copolymer produced in small wall thickness as by blow molding or a synthetic rubber such as ethylene-propylene rubber or silicone rubber may be used for the balloon 10, and a thermoplastic resin such as polyvinyl chloride, polypropylene, polystyrene, or polycarbonate may be used for the three-way adapter. During the insertion of the balloon 10 to the portion of the blood vessel in trouble, it is advanced inside the blood vessel as folded over itself so as to wrap up the middle tube 2. For the purpose of preventing the folded balloon from inflicting injury to the inner wall of the blood vessel during the course of the insertion inside the blood vessel and also for the purpose of enabling the balloon to be easily folded, the material of the balloon is desired to possess lower hardness than the material of the triple-flow catheter tube. Further, in the vasodilating catheter of the present invention, the portions thereof which are destined to contact the body fluid or the tissue of the vessel, i.e. the outer surface of the outer tube 3, the outer surface of the balloon 10, and the inner surface of the inner tube 1 are desired to have undergone a treatment for impartation of hydrophilicity so as to ensure lubricity of contact with the blood and smoothness of insertion in the blood vessel. This treatment for impartation of hydrophilicity can be attained, for example, by coating the specified surfaces with a hydrophilic polymer such as poly(2-hydroxyethyl methacrylate), polyhydroxyethyl acrylate, hydroxypropyl cellulose, methyl vinyl ether-maleic anhydride copolymer, polyethylene glycol, polyacrylamide, or polyvinyl pyrrolidone.

Now, a typical method by which the vasodilating catheter of the present invention is utilized for angioplasty will be described below with reference to the embodiment illustrated in FIG. 1 through FIG. 4.

In preparation for the angioplasty, the air remaining inside the vasodilating catheter must be removed. In the case of the vasodilating catheter of the embodiment, the vasodilating catheter is held with the leading end side thereof directed upwardly and the contrast medium is injected through the injection port 9, passed through the third flow path C and then led through the lateral hole 11 into the inner space D of the balloon 10. The interior of the balloon 10 is filled with the contrast medium from the basal end side of the catheter tube 4 upwardly. The air inside the balloon 10 is discharged through the lateral hole 12 as the contrast medium fills the balloon 10. Then, the air is passed through the second flow path B and released through the vent port 8 into the ambient air. When the inner space D of the balloon 10 is filled to capacity with the contrast medium, the incoming contrast medium overflows the balloon via the lateral hole 12 into the second flow path B and is released from the vent port 8. This release of the overflowing contrast medium completes the removal of air from within the vasodilating catheter and serves as a sign indicative of completion of the removal of air. Finally, as soon as the contrast medium begins to flow out of the vent port 8, the injection of the contrast medium is stopped and the vent port 8 is closed with a suitable stopper (not shown). Then the unnecessary contrast medium remaining in the inner space D is discharged by means of a syringe (not shown) so as to cause the balloon 10 to be wrapped on the middle tube 10 shrunken as much as possible, in preparation for the insertion of blood vessel by the angioplasty.

Figure 9:
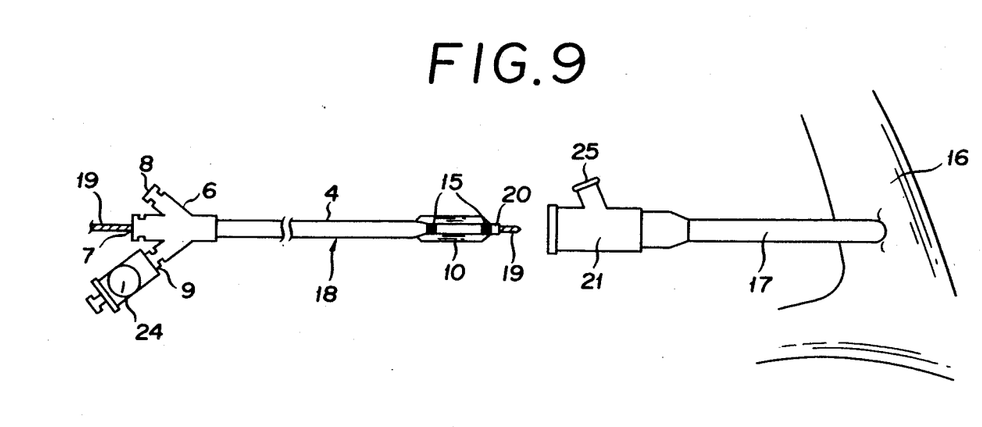
FIG. 9 through FIG. 13 are model diagrams illustrating the manner in which a typical vasodilating catheter as one embodiment of this invention is put to use.
Figure 10:
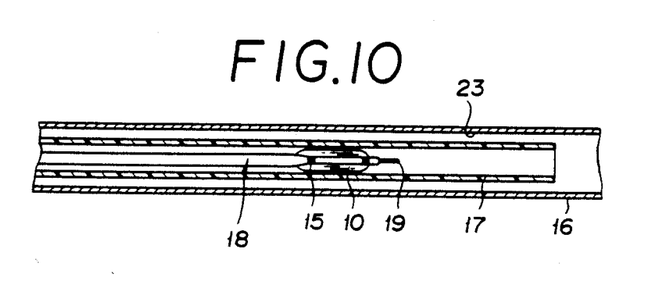
Figure 11:
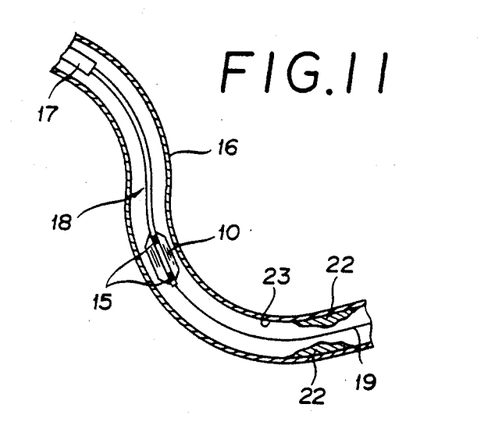
Figure 12:
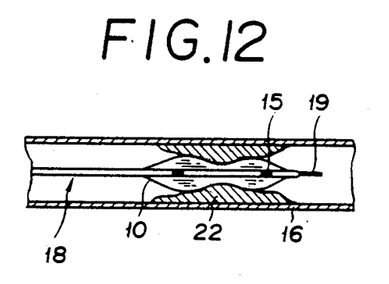
Figure 13:
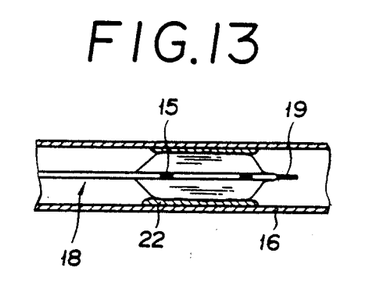

The angioplasty is started, as illustrated in FIG. 9, by first securing the blood vessel 16 on the patient's side as by the Seldinger method, then setting a guide wire (not shown) for the guide catheter within the blood vessel, inserting the guide catheter 17 along the guide wire, setting the inserted guide catheter 17 at the entrance of the coronary artery involving the diseased portion, and extracting the guide wire (not shown), subsequently inserting a guide wire 19 for the vasodilating catheter via the guide wire port 7 of the vasodilating catheter 18 into the inner tube 1 of the triple-flow catheter tube 4 until the leading end thereof thrusts out several centimeters from the opening 20 at the leading end of the inner 1, and allowing the protruding portion of the guide wire 19 to enter the guide catheter 17 through the medium of a Y-shaped connector 21 connected to the basal end of the guide catheter 17. FIG. 10 illustrates the state in which the guide catheter 17 and the vasodilating catheter 18 are held inside the blood vessel. Inside the blood vessel 16, the interior of the guide catheter 17 is filled with the blood which has entered via the leading end thereof. When the outer surface of the vasodilating catheter 18 has been treated for the impartation of hydrophilicity as described above, it exhibit lubricity to the contact as with the blood. Thus, the vasodilating catheter 18 smoothly advances inside the guide catheter 17. Then, the vasodilating catheter 18 departs from the leading end of the guide catheter 17 and advances into the blood vessel involving the diseased portion. Then, the guide wire 19 for the vasodilating catheter is extended inside the blood vessel toward the lesion as illustrated in FIG. 11. It is set in position after it has passed a portion of stenosis 22. Now, the vasodilating catheter 18 is advanced along the guide wire 19 for the vasodilating catheter into the blood vessel. In this case, there is possibility of the vasodilating catheter 18 coming into contact with the wall 23 of the blood vessel. When the outer surface of the vasodilating catheter 18 has undergone the treatment for impartation of hydrophilicity as described above, the vasodilating catheter 18 is allowed by the lubricity to advance smoothly inside the blood vessel without inflicting injury to the wall 23 of the blood vessel. With the aid of the markers 15 disposed inside the balloon 10 and detected by X-ray, the vasodilating catheter 18 is advanced until the balloon 10 will be located at the portion of stenosis 22 as illustrated in FIG. 12. At this position, the balloon is retained. When the balloon 10 reaches the stenotic portion 22, an injector 24 provided with a pressure gauge and connected to the injection port 9 generates pressure approximately in the range of several to ten atmospheres to feed a deaerated contrast medium into the balloon 10 and inflate the balloon 10 as illustrated in FIG. 13 and press and enlarge the stenotic portion 22. After this step of operation is completed, the contrast medium is injected into the blood vessel through an contrast medium injection port 25 of the Y-shaped connector 21 connected to the basal end of the guide catheter 17 to permit observation of the flow of blood on the peripheral side of the blood vessel by means of X-ray. When this observation has confirmed necessary improvement in the flow of blood through the blood vessel, the vasodilating catheter 18 and the guide wire 19 for vasodilating catheter are extracted from within the blood vessel and the guide catheter 17 is likewise extracted and the puncture in the blood vessel is stopped by pressure to complete the whole operation of angioplasty. Industrial Applicability:

As described above, the present invention is directed to a vasodilating catheter which is characterized by comprising a triple-flow catheter tube composed of an inner tube opening at the leading end thereof and defining a first flow path, a middle tube encircling the inner tube and defining a second flow path jointly with the inner tube, and an outer tube encircling the middle tube and defining a third flow path jointly with the middle tube, an at least partially cylindrical foldable balloon attached to the outer periphery of the catheter tube so as to enclose therewith the openings of the second flow path and the third flow path in the proximity of the leading end of the catheter tube and form a space-communicating with the second flow path and the third flow path, and three ports communicating with the three flow paths mentioned above, attached to the basal end of the catheter tube. When a stenosis or an obstruction occurs in the blood vessel, therefore, this invention can be advantageously used in the operation of angioplasty which is performed for widening the stenotic portion or reopening the obstructed portion and ensuring improved flow of blood on the peripheral side of the blood vessel. Particularly, the fact that the air remaining within the balloon can be easily removed enables the otherwise inevitable degradation of the opacifying property of the balloon due to persistence of bubbles in the introduced contrast medium to be precluded, the recognition of the position and the shape of the balloon to be effected easily, the treatment of the portion in trouble to be performed accurately, and the injury inflicted on the inner wall of the blood vessel owing to excessive extension of the blood vessel to be effectively prevented. Further, since one of the flow paths formed by the triple-flow catheter tube is adopted as a conduit for the discharge of the bubbles, the vasodilating catheter of this invention possesses more flexibility than the conventional vasodilating catheter and has only a sparing possibility of inflicting injury upon the inner wall of the blood vessel even when the blood vessel under treatment happens to abound with bends. Thus, the vasodilating catheter of the present invention enables the operation of angioplasty to be performed more safely, easily, and accurately and brings about a significant advance in the treatment of vascular disorders such as vasostenosis and arteriosclerosis obliterans.

Further in the vasodilating catheter of the present invention, when the opening of the second flow path is disposed in the proximity of one end part of the balloon and the opening of the third flow path in the proximity of the other end part of the balloon, and more desirably when the opening of the second flow path is disposed in the proximity of the end part of the balloon on the leading end side of the catheter tube and the opening of the third flow path in the proximity of the end part of the balloon on the basal end side of the catheter tube, the discharge of the air remaining inside the balloon can be attached more easily and accurately. When the middle tube is provided on the inner peripheral surface thereof with at least one protuberance and the inner tube the middle tube, and the outer tube of the triple-flow catheter tube are disposed coaxially relative to one another, the flow defined by the three tubes can be formed more conveniently. When the rigidity of the balloon is smaller than that of the triple-wall catheter tube, the inflation and contraction of the balloon can be effected more desirably. Further when the outer surface of the outer tube, the outer surface of the balloon, and the inner surface of the inner tube have been given a treatment for impartation of hydrophilicity, the vasodilating catheter can be used advantageously because the advance of the vasodilating catheter within the blood vessel proceeds smoothly and the possibility of the vasodilating catheter inflicting injury on the inner wall of the blood vessel is lessened.

We claim:
1. A vasodilating catheter, comprising:
a triple-flow catheter tube having a leading end and a basal end, and comprising an inner tube opening at a leading end thereof and defining a first flow path, a middle tube encircling said inner tube and defining a second flow path jointly with said inner tube, and an outer tube encircling said middle tube and defining a third flow path jointly with said middle tube,
an at least partially cylindrical foldable balloon attached to the outer periphery of said triple-flow catheter tube so as to enclose therewith openings of said second flow path and said third flow path in the proximity of the leading end of said triple-flow catheter tube and to form a space communicating with said second flow path and said third flow path, and three ports communicating with said three flow paths, attached to the basal end of said triple-flow catheter tube.

2. A vasodilating catheter according to claim 1, wherein the opening of said second flow path is in the proximity of one end of said balloon, and the opening of said third flow path in the proximity of the other end of said balloon.

3. A vasodilating catheter according to claim 1, wherein the opening of said second flow path is in the proximity of said catheter tube's leading end side terminal of said balloon, and the opening of said third flow path is in the proximity of said catheter tube's leading end side terminal of said balloon.

4. A vasodilating catheter according to claim 1, wherein said middle tube is provide on the inner peripheral surface thereof with at least one protuberance contiguous to the outer peripheral surface of said inner tube.

5. A vasodilating catheter according to claim 1, wherein:
the leading end of said middle tube is tapered to a diameter equal to or slightly smaller than the outside diameter of said inner tube and fitted into said inner tube and fastened thereto, and
said second flow path communicates with said balloon through the medium of at least one lateral hole formed in said middle tube near the leading end thereof.

6. A vasodilating catheter according to claim 1, wherein:
the leading end of said outer tube is tapered to a diameter equal to or slightly smaller than the outside diameter of said middle tube and fitted into said middle tube and fastened thereto, and
said third flow path communicates with said balloon through the medium of at least one lateral hole formed in said outer tube near the leading end thereof.

7. A vasodilating catheter according to claim 1, wherein said inner tube, said middle tube, and said outer tube of said triple-flow catheter tube are disposed coaxially relative to one another.

8. A vasodilating catheter according to claim 1, wherein said triple-flow catheter tube and said balloon are formed with thermoplastic resin.

9. A vasodilating catheter according to claim 1, wherein the hardness of said balloon is lower than that of said triple-flow catheter tube.

10. A vasodilating catheter according to claim 1, wherein the outer surface of said outer tube, the outer surface of said balloon, and the inner surface of said inner tube and treated for impartation of hydrophilicity.

11. A vasodilating catheter according to claim 5, wherein said leading end of said middle tube is fastened to said inner tube with an adhesive agent.

12. A vasodilating catheter according to claim 5, wherein said leading end of said middle tube is fastened to said inner tube by thermal fusion.

13. A vasodilating catheter according to claim 6, wherein said leading end of said outer tube is fastened to said inner tube with an adhesive agent.

14. A vasodilating catheter according to claim 6, wherein said leading end of said middle tube is fastened to said inner tube by thermal fusion.

15. A vasodilating catheter according to claim 2, wherein said inner tube, said middle tube, and said outer tube of said triple-flow catheter tube are disposed coaxially relative to one another.

16. A vasodilating catheter according to claim 3, wherein said inner tube, said middle tube, and said outer tube of said triple-flow catheter tube are disposed coaxially relative to one another.

17. A vasodilating catheter according to claim 4, wherein said inner tube, said middle tube, and said outer tube of said triple-flow catheter tube are disposed coaxially relative to one another.

18. A vasodilating catheter according to claim 5, wherein said inner tube, said middle tube, and said outer tube of said triple-flow catheter tube are disposed coaxially relative to one another.

19. A vasodilating catheter according to claim 6, wherein said inner tube, said middle tube, and said outer tube of said triple-flow catheter tube are disposed coaxially relative to one another.

* * * * *

UNITED STATES PATENT AND TRADEMARK OFFICE
CERTIFICATE OF CORRECTION

PATENT NO. : 4,955,895

DATED : September 11, 1990

INVENTOR(S) : SUGIYAMA et al

It is certified that error appears in the above-identified patent and that said Letters Patent is hereby corrected as shown below:

TITLE PAGE:

Under Section [56] Cited References, after "U.S. Patent Documents", insert:

--FOREIGN PATENT DOCUMENTS:

59-177064  10/1984  Japan--

Signed and Sealed this

Second Day of June, 1992

*Attest:*

DOUGLAS B. COMER

*Attesting Officer*     *Acting Commissioner of Patents and Trademarks*